United States Patent [19]

Dockner et al.

[11] Patent Number: 4,767,856

[45] Date of Patent: Aug. 30, 1988

[54] PREPARATION OF CAPROLACTAM FROM 6-AMINOCAPROIC ACID, ESTERS AND AMIDES

[75] Inventors: Toni Dockner, Meckenheim; Manfred Sauerwald, Roedersheim-Gronau; Rolf Fischer, Heidelberg; Hans-Martin Hutmacher, Ludwigshafen; Claus-Ulrich Priester, Meckenheim; Uwe Vagt, Speyer, all of Fed. Rep. of Germany

[73] Assignee: BASF Aktiengesellschaft, Ludwigshafen, Fed. Rep. of Germany

[21] Appl. No.: 133,274

[22] Filed: Dec. 15, 1987

[30] Foreign Application Priority Data

Dec. 17, 1986 [DE] Fed. Rep. of Germany ....... 3643011

[51] Int. Cl.$^4$ ........................................... C07D 201/08
[52] U.S. Cl. ................................................ 540/538
[58] Field of Search ......................................... 540/538

[56] References Cited

U.S. PATENT DOCUMENTS 3,485,821 12/1969 Sheehan ............................. 540/538
3,857,510 12/1974 Rogic et al. ........................ 540/538
3,988,319 10/1976 Mares .................................. 540/538
4,470,928 9/1984 Kimura et al. ...................... 540/538
4,551,528 11/1985 Dockner et al. ................... 540/538

FOREIGN PATENT DOCUMENTS 2249993 10/1972 Fed. Rep. of Germany ...... 540/538
3235938 4/1982 Fed. Rep. of Germany ...... 540/538

OTHER PUBLICATIONS

Industrial & Engineering Chemistry Process Design and Development vol. 17, No. 1, 1978, Mares and Sheehan, Kinetics of Caprolactam Formation from 6-Aminocaproic Acid, Ester, and Amides.

Primary Examiner—Robert T. Bond
Attorney, Agent, or Firm—Keil & Weinkauf

[57] ABSTRACT

In an improved process for preparing caprolactam by heating 6-aminocaproic acid, an ester or amide or mixture thereof in the presence of an inert reaction medium which is liquid under the reaction conditions and has a boiling point above that of caprolactam, the improvement comprises using as the reaction medium a hydrocarbon, maintaining a temperature of from 150° to 350° C., charging the 6-aminocaproic acid, ester, amide or mixture thereof at a rate commensurate with their rate of conversion, and separating caprolactam from the reaction mixture at a rate commensurate with its rate of formation.

10 Claims, No Drawings

PREPARATION OF CAPROLACTAM FROM 6-AMINOCAPROIC ACID, ESTERS AND AMIDES

The present invention relates to a process for preparing caprolactam from 6-aminocaproic acid, esters and amides and also mixtures thereof.

German Laid-Open Application DOS No. 2,249,993 describes a process wherein 6-aminocaproic esters are converted at 250°–350° C. in the presence of water into caprolactam. However, the process has the disadvantage that the conversion has to be carried out under superatmospheric pressure. In addition, the cyclization should be carried out at lower concentrations to suppress the formation of oligomers. As a consequence, it is technically complicated to isolate the caprolactam from the dilute solution. In another process, described in German Laid-Open Application DOS No. 3,235,938, 6-aminocaproic esters are converted into caprolactam by heating at from 180° to 250° C. for a period of from 0.5 to 5 hours in a polyhydric alcohol having a boiling point higher than that of caprolactam, and subsequently the caprolactam is separated by distillation from the reaction mixture obtained. This process has the disadvantage that, again, relatively dilute solutions from 5 to 15% by weight are supposed to be used and, what is more, that demanding solvents, such as tetraethylene glycol, which need to be recovered, are employed. Finally, isolating the caprolactam in two separate stages is inconvenient.

Ind. Eng. Chem. Process Des. Dev., 17 (1978), 9, describes the cyclization of 6-aminocaproamide in ethanol and water at 180°–250° C. to form caprolactam. However, substantial amounts of dimers are formed as by-products, so that the yield leaves something to be desired.

It is an object of the present invention to provide a process for preparing caprolactam from 6-aminocaproic acid, esters, amides or mixtures thereof in high yield under atmospheric pressure in a short time without expensive solvent but with simple isolation of the caprolactam.

We have found that this object is achieved in a process for preparing caprolactam by heating 6-aminocaproic acid, an ester or amide or mixture thereof in the presence of an inert reaction medium which is liquid under the reaction conditions and has a boiling point above that of caprolactam, wherein the reaction medium used is a hydrocarbon, a temperature from 150° to 350° C. is maintained, the 6-aminocaproic acid, ester, amide or mixture thereof is charged at a rate commensurate with the rate of conversion, and the caprolactam is separated from the reaction mixture at a rate commensurate with its rate of formation.

The novel process has the advantage that it proceeds under atmospheric pressure with high conversion and in high yields, no expensive solvents need to be present and consequently the recovery of solvent is dispensed with. Moreover, the novel process has the advantage that the isolation of caprolactam takes a simple form.

The novel process is remarkable insofar as it is expressly pointed out on pages 18 and 19 of said DOS No. 3,235,938 that, if aminocaproic esters are converted in hydrocarbon solvents, an insoluble polymer is formed.

Preferred starting materials comprise those of the general formula I

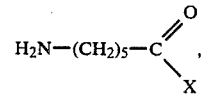

where X is OH, OR$^1$, where R$^1$ is alkyl, cycloalkyl or aralkyl, or

where R$_2$ and R$_3$ can be identical or different and each is hydrogen or alkyl of 1 to 4 carbon atoms, and R$_2$ and R$_3$, together with the nitrogen atom on which they are substituents, can form a 5- to 7-membered ring.

Suitable starting materials are for example 6-aminocaproic acid and esters thereof with C$_1$–C$_{10}$-alkanols, cycloalkanols of 3 to 10 carbon atoms or aralkanols of 7 to 10 carbon atoms. Of the esters, C$_1$–C$_4$-alkyl 6-aminocaproates are preferred. Also suitable are 6-aminocaproamide and C$_1$–C$_4$-alkyl-substituted derivatives thereof.

Preferred 6-aminocaproic esters comprise those with ethanol, n-propanol, i-propanol, n-butanol or sec.-butanol as the alcohol component. Methyl 6-aminocaproate and ethyl 6-aminocaproate are particularly preferred.

Preference is also given to 6-aminocaproic amide, dimethylamide or diethylamide.

The starting materials used can be used not only in a pure form but also in the form of an aqueous or alcoholic solution. If an ester is used, the alcohol used as the solvent advantageously corresponds to the alcohol component of the ester.

The reaction is carried out at from 150° to 350° C., advantageously from 250° to 330° C. In general, atmospheric pressure is employed, but it is also possible to carry out the reaction under reduced pressure, for example down to 10 mbar.

According to the invention, the reaction is carried out in a reaction medium comprising a liquid hydrocarbon which is inert under the reaction conditions. The hydrocarbon used has a higher boiling point than the caprolactam to be prepared. Advantageously, the hydrocarbon used has a boiling point of not less than 300° C., in particular from 350° to 550° C. Suitable hydrocarbons are for example mineral oil fractions of appropriate boiling point, in particular technical-grade white oil, vacuum gas oil, vacuum residue oil, heavy heating oil, molten paraffin wax, aromatic hydrocarbon oil or Marlotherm oil.

Advantageously, the reaction is carried out in the presence of an acid catalyst. Suitable catalysts are, for example, phosphoric acid, diphenylphosphinic acid, dodecylbenzenesulfonic acid and supported acid catalysts, for example phosphoric acid on silica gel. The catalyst is advantageously added to the reaction medium in an amount from 0.1 to 10% by weight.

According to the invention, the starting materials are introduced into the hot hydrocarbon at reaction temperature at a rate commensurate with that of their consumption. Advantageously, the 6-aminocaproic acid, ester, amide or mixture thereof is introduced into the hydrocarbon at a rate from 0.01 to 1.0 kg/h per liter thereof. Advantageously, an inert gas such as nitrogen or carbon dioxide, in particular nitrogen, is introduced in addition. It is of proven utility to employ from 0.01 to 0.2 m$^3$ (S.T.P.) of inert gas per liter of hydrocarbon.

An adjunct to the reaction is a product separation step, in which the caprolactam is removed from the reaction mixture, for example by distillation or stripping with the inert gas, at a rate commensurate with its rate of formation. At the same time, other low-boiling compounds, for example freed water, freed alcohol or freed amines, unconverted starting materials and also small amounts of volatile constituents are removed from the solvent in gas form. In this way the concentration of 6-aminocaproic acid, esters or amides and also caprolactam in the hot hydrocarbon is kept to a minimum. The resulting vapors which, in addition to the inert gas, contain caprolactam and the aforementioned substances, are subsequently condensed and advantageously charged to a distillation column, where the caprolactam is separated off.

The reaction is carried out, for example, in stirred vessels or cylindrical reactors or packed columns. The apparatus is advantageously filled up to two thirds with the inert hydrocarbon reaction medium, which may contain a catalyst. The starting materials are advantageously introduced to the reactor at the bottom end, using if desired an inert gas such as nitrogen as stripping gas. The liquid reaction mixture is maintained at the abovementioned temperature, and the discharged products are condensed and separated by distillation. Small amounts of sparingly volatile by-products remain behind in the hydrocarbon and are advantageously bled out by partial takeoff of the hydrocarbon, and the reactor contents are replenished with fresh hydrocarbon. The hydrocarbon takeoff is not recovered but advantageously used for undergrate firing.

Caprolactam is used for producing polycaprolactam.

The process according to the invention is illustrated by reference to the following Examples.

EXAMPLE 1

A 2-liter stirred flask was charged with 900 g of technical-grade white oil and heated to 250° C. Per hour, 73 g of methyl 6-aminocaproate were introduced at the bottom end together with 110 l (S.T.P.) of nitrogen. The gaseous products leaving the reaction vessel were cooled down, and the condensate was analyzed by gas chromatography. A 4-hour run produced 295 g of condensate which, according to analysis by gas chromatography, contained 6.4 g of unconverted methyl 6-aminocaproate and 220.6 g of caprolactam. This corresponds to a conversion of 97.8% and a selectivity of 99.1%.

EXAMPLE 2

A 2-liter stirred flask was charged with 900 g of technical-grade white oil and heated to 250° C. Per hour, 76 g of a 61% strength solution of methyl 6-aminocaproate in methanol were introduced at the bottom end together with 50 l (S.T.P.) of nitrogen. The gaseous products leaving the reaction vessel were condensed. In a 4-hour run, a total of 304 g of the solution, corresponding to 185.4 g of methyl 6-aminocaproate, were made to react to give 292 g of condensate which, according to analysis by gas chromatography, contained 10.7 g of unconverted methyl 6-aminocaproate and 132.7 g of caprolactam. This corresponds to a conversion of 94.2% and a selectivity of 97.5%.

EXAMPLE 3

A 2-liter stirred flask was charged with 900 g of vacuum gas oil and heated to 300° C. Per hour, 49 g of a 67% strength solution of methyl 6-aminocaproate in methanol were introduced at the bottom end together with 50 l (S.T.P.) of nitrogen. The gaseous products leaving the reaction vessel were condensed. In a 3-hour run, a total of 147 g of the solution, corresponding to 98.5 g of methyl 6-aminocaproate, were made to react to give 154 g of condensate which, according to analysis by gas chromatography, contained 5.8 g of unconverted methyl 6-aminocaproate and 70.5 g of caprolactam. This corresponds to a conversion of 94.1% and a selectivity of 97.6%.

EXAMPLE 4

A 2-liter stirred flask was charged with 900 g of technical-grade white oil and 10 g of diphenylphosphinic acid and heated to 300° C. Per hour, 87 g of a 57% strength solution of methyl 6-aminocaproate in methanol were introduced at the bottom end together with 50 l (S.T.P.) of nitrogen. The gaseous products leaving the reaction vessel were condensed. In the course of a 3-hour run, a total of 261 g of the solution, corresponding to 148.8 g of methyl 6-aminocaproate, were made to react to give 262 g of a condensate which, according to analysis by gas chromatography, contained 0.7 g of unconverted methyl 6-aminocaproate and 106.1 g of caprolactam. This corresponds to a conversion of 99.5% and a selectivity of 91.9%.

EXAMPLE 5

A 2-liter stirred flask was charged with 900 g of technical-grade white oil and heated to 250° C. Per hour, 80 g of ethyl 6-aminocaproate were introduced at the bottom end together with 110 l (S.T.P.) of nitrogen. The gaseous products leaving the reaction vessel were condensed. A 4-hour run produced 325 g of a condensate which, according to analysis by gas chromatography, contained 8.0 g of unconverted ethyl 6-aminocaproate and 219.4 g of caprolactam. This corresponds to a conversion of 97.5% and a selectivity of 98.9%.

EXAMPLE 6

A 2-liter stirred flask was charged with 900 g of technical-grade white oil and heated to 250° C. Per hour, 100 g of a 30% strength aqueous solution of 6-aminocaproic acid were introduced at the bottom end. The gaseous products leaving the reaction vessel were condensed. In the course of a 3-hour run, a total of 300 g of the solution, corresponding to 90 g of 6-aminocaproic acid, were made to react to give 280 g of a condensate which, according to analytical gas chromatography, contained 56.8 g of caprolactam but no starting material. The quantitative conversion is coupled with a selectivity of 73.1%.

EXAMPLE 7

A 2-liter stirred flask was charged with 900 g of technical-grade white oil and heated to 300° C. Per hour, 65 g of 6-aminocaproic acid were introduced together with 110 l (S.T.P.) of nitrogen. The gaseous products leaving the reaction vessel were condensed. A 4-hour run produced 231 g of a condensate which, according to analytical gas chromatography, contained 190.9 g of caprolactam but no starting material. The quantitative conversion is coupled with a selectivity of 85.1%.

EXAMPLE 8

A 2-liter stirred flask was charged with 900 g of technical-grade white oil and heated to 300° C. Per hour, 65 g of 6-aminocaproamide were introduced together with 110 l (S.T.P.) of nitrogen. The gaseous products leaving the reaction vessel were condensed, and the condensate was analyzed by gas chromatography. A 4-hour run produced 225 g of a condensate which, according to analysis by gas chromatography, contained 215.8 g of caprolactam but no starting material. The quantitative conversion was coupled with a selectivity of 95.5%.

EXAMPLE 9

A heatable tube 60 mm in internal diameter and 1500 mm in length was charged with 2000 g of technical-grade white oil and heated to 300° C. Per hour, 145 g of methyl 6-aminocaproate were introduced at the bottom end together with 110 l (S.T.P.) of nitrogen. At the top of the tube the gaseous products were drawn off, and cooled down, and the condensate was analyzed by gas chromatography. A 4-hour run produced 595 g of a condensate which, according to analysis by gas chromatography, contained 2.1 g of unconverted methyl 6-aminocaproate and 446.8 g of caprolactam. This corresponds to a conversion of 99.6% and a selectivity of 99.2%.

We claim:

1. An improved process for preparing caprolactam by heating 6-aminocaproic acid, an ester or amide thereof, or a mixture thereof, in the presence of an inert reaction medium which is liquid under the reaction conditions and has a boiling point above that of caprolactam, wherein the improvement comprises using as the reaction medium a hydrocarbon, maintaining a temperature of from 150° to 350° C., charging the 6-aminocaproic acid, ester, amide or mixture thereof at a rate commensurate with the rate of conversion, and separating caprolactam from the reaction mixture at a rate commensurate with its rate of formation.

2. A process as claimed in claim 1, wherein the hydrocarbon used has a boiling point from 350° to 550° C.

3. A process as claimed in claim 1, wherein a temperature from 250°0 to 330° C. is maintained.

4. A process as claimed in claim 1, wherein per hour from 0.01 to 1.0 kg of aminocaproic acid, ester, amide or mixture thereof is introduced into the hydrocarbon per liter thereof.

5. A process as claimed in claim 1, wherein an inert gas is introduced in addition.

6. A process as claimed in claim 1, wherein reduced pressure is employed.

7. A process as claimed in claim 1, wherein an acid catalyst is additionally present.

8. A process as claimed in claim 1, wherein the starting compound is methyl 6-aminocaproate or ethyl 6-aminocaproate.

9. A process as claimed in claim 1, wherein the starting material used is 6-aminocaproamide which may be substituted on the nitrogen atom by methyl or ethyl.

10. A process as claimed in claim 1, wherein a portion of the hydrocarbon containing sparingly volatile by-products is bled out and replaced by fresh hydrocarbon and the hydrocarbon bleedout is used for undergrate firing.

* * * * *